(12) United States Patent
Farzadfard

(10) Patent No.: US 10,039,570 B2
(45) Date of Patent: Aug. 7, 2018

(54) ORTHOPEDIC DEVICE FOR CLOSED FRACTURE REDUCTION

(71) Applicant: Hamid Farzadfard, Mashhad (IR)

(72) Inventor: Hamid Farzadfard, Mashhad (IR)

( * ) Notice: Subject to any disclaimer, the term of this patent is extended or adjusted under 35 U.S.C. 154(b) by 0 days.

(21) Appl. No.: 15/362,839

(22) Filed: Nov. 29, 2016

(65) Prior Publication Data

US 2017/0119436 A1     May 4, 2017

Related U.S. Application Data

(60) Provisional application No. 62/265,459, filed on Dec. 10, 2015.

(51) Int. Cl.
*A61B 17/66* (2006.01)
*A61B 17/88* (2006.01)
*A61B 17/56* (2006.01)

(52) U.S. Cl.
CPC ........ *A61B 17/66* (2013.01); *A61B 2017/564* (2013.01)

(58) Field of Classification Search
CPC .......................... A61B 17/66; A61B 2017/564
USPC .......... 606/55, 57, 59, 62–68, 86 R, 90, 105
See application file for complete search history.

(56) References Cited

U.S. PATENT DOCUMENTS

| | | | | |
|---|---|---|---|---|
| 2,250,417 A * | 7/1941 | Ettinger | ................. | A61B 17/60 606/54 |
| 4,913,137 A * | 4/1990 | Azer | ................. | A61B 17/1725 606/64 |
| 5,624,447 A * | 4/1997 | Myers | ................. | A61B 17/1717 606/104 |
| 6,328,737 B1 | 12/2001 | Moorcroft et al. | | |
| 7,727,240 B1 * | 6/2010 | Benton | ................. | A61B 17/1707 606/62 |
| 2004/0097922 A1 * | 5/2004 | Mullaney | ........... | A61B 17/6458 606/53 |
| 2004/0133199 A1 | 7/2004 | Coati | | |
| 2010/0076498 A1 * | 3/2010 | Tyber | ................. | A61B 17/8625 606/302 |
| 2015/0112344 A1 * | 4/2015 | Shoham | ............. | A61B 17/1703 606/64 |

OTHER PUBLICATIONS

P. Reynders, Unreamed intramedullary nailing of femoral shaft fractures using a traction device, Injury, Jan. 1998, vol. 29, Issue 1, pp. 81-84.

(Continued)

*Primary Examiner* — Pedro Philogene
*Assistant Examiner* — David C Comstock
(74) *Attorney, Agent, or Firm* — Bajwa IP Law Firm; Haris Zaheer Bajwa

(57) ABSTRACT

A fracture reduction device for reducing a fractured bone having a proximal fragment and a distal fragment may include: a proximal attachment member that may be configured to be coaxially attached and fixed into the proximal fragment of the bone; a distal attachment member that may be configured to be laterally attached and fixed to the distal fragment of the bone; and a distracting mechanism that may engage with the proximal attachment member and be coupled with the distal attachment member. The distracting mechanism may be configured to manipulate the proximal fragment and the distal fragment to restore their alignment and orientation.

14 Claims, 11 Drawing Sheets

(56) References Cited

OTHER PUBLICATIONS

G De Bastian, The treatment of fractures with a dynamic axial fixator, Bone & Joint Journal, Aug. 1984, vol. 66, Issue 4, pp. 538-545.
Amal Khoury, Computerized fluoroscopic-based navigation-assisted intramedullary nailing, American journal of orthopedics, 2007, vol. 36, Issue 11, pp. 582-585.

* cited by examiner

ORTHOPEDIC DEVICE FOR CLOSED FRACTURE REDUCTION

CROSS REFERENCE TO RELATED APPLICATION

This application claims the benefit of priority from U.S. Provisional Patent Application Ser. No. 62/265,459, filed on Dec. 10, 2015, and entitled "CLOSE REDUCTION SET FOR LONG BONE FRACTURES," which is incorporated herein by reference in its entirety.

TECHNICAL FIELD

The present disclosure generally relates to orthopedic tools, and more particularly to an orthopedic device for bone relocation and fracture reduction in long bones.

BACKGROUND

Reduction is a surgical procedure to restore a fracture or dislocation to the correct alignment. When a bone fractures, the fragments lose their alignment in the form of displacement or angulation. For the fractured bone to heal without any deformity the bony fragments must be re-aligned to their normal anatomical position. Orthopedic surgery attempts to recreate the normal anatomy of the fractured bone by reduction of the displacement or the fracture.

After reduction, the reduced fracture must be fixed. Fracture fixation is carried out for stabilizing the reduced fractured bone in order to enable fast healing of the injured bone, and to return early mobility and full function of the injured extremity.

Fracture reduction is carried out by either closed or open methods. In open reduction, the fracture fragments are exposed surgically by dissecting the tissue. While in closed reduction, the bone fragments are reduced without surgical exposure of the fragments. In the closed reduction method, bone fragments are indirectly manipulated by different methods, such as, traction of the whole limb on a fracture table or using hanging weights; or distraction of bone fragments indirectly, using mechanical distractors attached to the bone fragments by some drilled pins through the skin far from the fracture site.

In closed reduction, the fixation is carried out by methods, such as, intramedullary fixation using intramedullary nailing, in which, the integrity of the fracture site soft tissue is preserved. There may be advantages in preserving the integrity of the soft tissue of the fracture site in terms of cosmetics, blood loss, and rate of union, time of surgery, rehabilitation and medical costs.

After reducing the long bone fractures, a common preferred fixation method may include internal splinting by intramedullary nails that are inserted into the bone medulla from one end of the fractured bone far from the fracture site. In this method one end of the bone medullary canal is opened and a guide wire is passed through the bone fixing and aligning the bone fractures in the required position. This is the critical stage of intramedullary nailing of a long bone especially femur, because of its large soft tissue mass.

Closed nailing method is often used for treatment of long bone fractures. In this method a fracture table for fastening the patient, a fluoroscopy set, and devices for bone manipulation to achieve bone reduction are needed.

In spite of all the devices and facilities used in closed nailing method, the method is time-consuming, since it takes a long time to pass the guide wire through the medullary canal as the initiating critical step of the surgery. Exposure of x-ray radiation to the patient and staff is also a disadvantage of the method.

Nowadays mechanical distractors are used for bone reduction, in which few pins are used for the attachment of the mechanical distractor to the bones near the fracture site in order to avoid any surgical incisions and using a fracture table.

There is, therefore, a need in the art for a distractor capable of distracting the bone parts dynamically, so that the distracted parts can be freely manipulated and fixed in the desired position for reduction.

SUMMARY

The following brief summary is not intended to include all features and aspects of the present application, nor does it imply that the application must include all features and aspects discussed in this summary.

In one general aspect, the present disclosure describes a fracture reduction device for reducing a fractured bone having a proximal fragment and a distal fragment. The device may include: a proximal attachment member that may be configured to be coaxially attached and fixed into the proximal fragment of the bone; a distal attachment member that may be configured to be laterally attached and fixed to the distal fragment of the bone; and a distracting mechanism that may engage with the proximal attachment member and be coupled with the distal attachment member. The distracting mechanism may be configured to manipulate the proximal fragment and the distal fragment to restore their alignment and orientation.

According to an implementation, the proximal attachment member may be configured as a cannulated screw that may have a cylindrical canal in the middle. The cylindrical canal may allow passage of a guide wire, and therefore the proximal attachment member may be screwed over the guide wire into the proximal fragment of the fractured bone.

According to another implementation, the proximal attachment member may further include a support. The support may be configured as an engagement point for the distracting mechanism to engage the proximal attachment member. The support may be formed integral with the cannulated screw.

According to some implementations, the cannulated screw may include a threaded segment in its distal end and a wrenching segment in its proximal end. The threaded segment may be configured to be screwed into the proximal segment of the bone, and the wrenching segment may be configured to allow for utilizing a driving means to drive the cannulated screw in to the proximal segment of the bone. According to another implementation, a tapper may be formed on the distal end of the cannulated screw.

According to some implementations, the distal attachment member may be configured as a plate with a number of holes thereon. The holes may be configured to allow for orthopedic screws to be driven into the distal fragment therethrough.

According to an implementation, the distracting mechanism may include: a distal manipulating handle that may be coupled with the distal fragment of the fractured bone via being coupled with the distal attachment member; an extendable body; and a proximal engagement member that may be configured to engage the proximal attachment member, and be attached to the proximal fragment via the proximal attachment member. The extendable body may include a fixed arm and an extendable arm adjustably movable inside the fixed arm allowing for telescopically changing the length of the distracting mechanism. The distal manipulating handle may be configured to be articulated with the extendable arm, thereby manipulate the distal fragment of the fractured bone. The proximal engagement member may be configured to be slideably attached to the fixed arm.

According to other implementations, the fixed arm may have an L-shaped configuration having a vertical portion and a horizontal portion. The vertical portion may be configured to telescopically receive the extendable arm therein, and the horizontal portion may be configured to receive the proximal engagement member therein.

According to an implementation, the extendable arm may be a threaded rod and the extendable body may further include an adjustment nut threaded on the extendable arm that may be configured to urge the extendable arm out of the fixed arm.

In another general aspect, a method for reducing fracture in a bone that may include steps of: opening a proximal canal in the bone; passing a guide wire through the proximal canal; attaching a proximal attachment member to a proximal fragment of the bone, where the proximal attachment member comprises a cannulated screw; attaching a distal attachment member to a distal fragment of the bone by utilizing at least two orthopedic screws; connecting the proximal attachment member and the distal attachment member to a distracting mechanism; and manipulating the distracting mechanism to restore alignment and orientation of a the proximal fragment and the distal fragment to a pre-fracture state.

BRIEF DESCRIPTION OF THE DRAWINGS

While the specification concludes with claims particularly pointing out and distinctly claiming the subject matter that is regarded as forming the present application, it is believed that the application will be better understood from the following description taken in conjunction with the accompanying DRAWINGS, where like reference numerals designate like structural and other elements, in which:

DETAILED DESCRIPTION

In the following detailed description, numerous specific details are set forth by way of examples in order to provide a thorough understanding of the relevant teachings. However, it should be apparent that the present teachings may be practiced without such details. In other instances, well known methods, procedures, components, and/or circuitry have been described at a relatively high-level, without detail, in order to avoid unnecessarily obscuring aspects of the present teachings.

For purposes of explanation, specific nomenclature is set forth to provide a thorough understanding of the present disclosure. However, it will be apparent to one skilled in the art that these specific details are not required to practice principles consistent with the present disclosure. Descriptions of exemplary embodiments are provided only as representative examples. Various modifications to the exemplary embodiments will be readily apparent to one skilled in the art, and the general principles defined herein may be applied to other implementations and applications without departing from the scope of the principles of the present disclosure. The present disclosure is not intended to be limited to the implementations shown, but is to be accorded the widest possible scope consistent with the principles and features disclosed herein.

Figure 1:
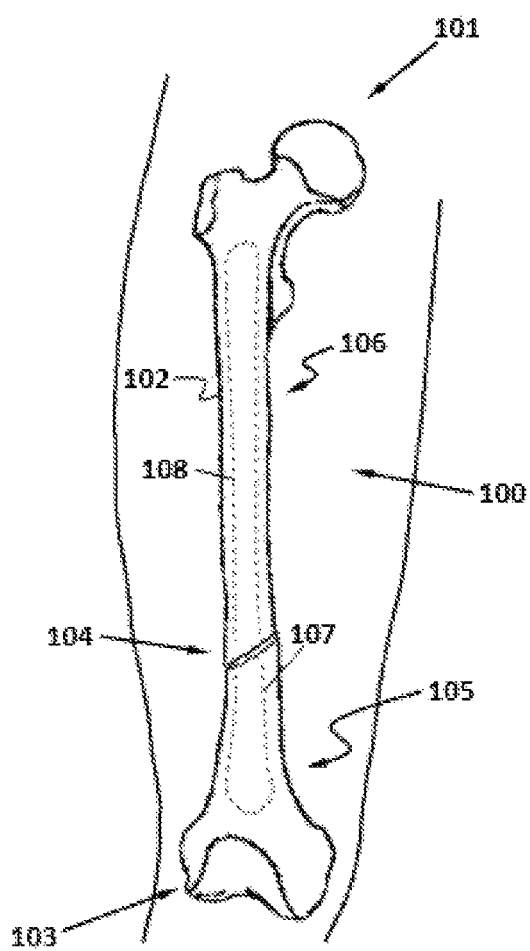
FIG. 1 shows an example of a fractured bone.

FIG. 1 illustrates femur bone 100 that may serve as an example of a long bone. Bone 100 may include proximal end 101, middle shaft 102, and distal end 103. Proximal end 101 may articulate with acetabulum in the pelvic bone to form the hip joint, while distal end 103 may articulate with the tibia and kneecap to form the knee joint. Fractures of femur shaft 102 may vary greatly, depending on the force that causes the break. Fragments of bone may line up correctly or be out of alignment, and the fracture may be closed (i.e., skin is intact) or open (i.e., the bone has punctured the skin). Femur shaft fractures are classified depending on: the location of the fracture (i.e., proximal, middle, or distal), the pattern of the fracture (e.g., the bone can break in different directions, such as cross-wise, length-wise, or in the middle), and whether the skin and muscle above the bone is torn by the injury. Two of the most common types of femoral shaft fractures include: transverse fracture, where the break is a straight horizontal line going across femoral shaft 102; and an oblique fracture, where the fracture has an angled line across shaft 102.

Referring to FIG. 1, the exemplary femur bone 100 has fracture 104 and two bone fragments, namely proximal fragment 106 having proximal medullary canal 108 and distal fragment 105 having distal medullary canal 107 may be created due to fracture 104.

Figure 2A:
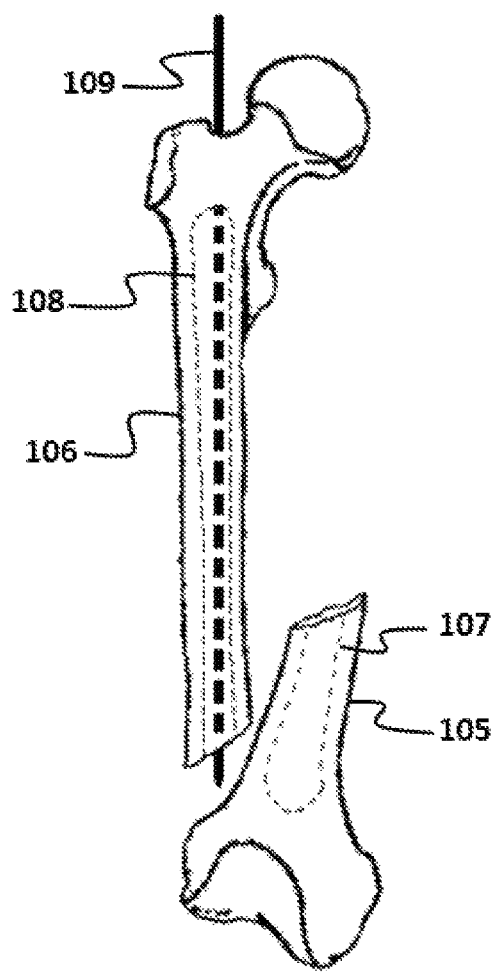
FIG. 2A shows an example of fractured femur bone, with overriding and angulated bone fragments.
Figure 2B:
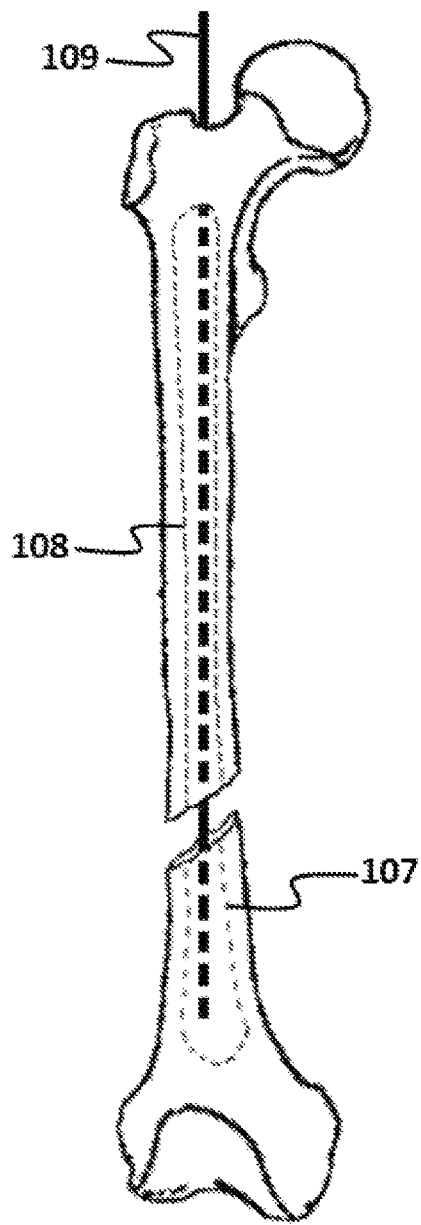
FIG. 2B shows fractured femur bone of FIG. 2A after reduction.

Referring to FIG. 2A, in a fractured bone, proximal fragment 106 and distal fragment 105 may lose their proper alignment and orientation under the initial deforming trauma force or later, under muscle contractions. In order to perform an intramedullary nailing surgery, proximal canal 108 may be opened by, for example, an awl and a starting reamer. Then, guide wire 109 may be inserted into proximal canal 108. After that, the alignment and orientation of fragments 106 and 105 may be restored by manipulating them, such that distal canal 107 and proximal canal 108 may be aligned and the guide wire 109 may pass through the proximal canal 108 into distal canal 107 as shown in FIG. 2B. Finally, a cannulated intramedullary nail may be mounted on guide wire 109 and inserted in to the intramedullary canal to achieve intramedullary nail fixation.

Disclosed herein are devices and methods directed to reducing bone fractures, i.e., manipulating bone fragments to restore their alignment and orientation. Devices and methods as described according to one or more aspects of the present disclosure may include a reduction device having a distracting mechanism, a proximal attachment mechanism and a distal attachment mechanism. In an aspect, the proximal attachment mechanism may be coaxially fixed to the proximal fragment of the fractured bone and the distal attachment mechanism may be fixed to the distal bone fragment. The distractor mechanism may be coupled with the proximal and the distal attachment mechanisms, such that the proximal and distal fragments may be manipulated by the distracting mechanism. The distracting mechanism, in an aspect, may be configured to manipulate the proximal and distal fragments of the fractured bone in order to restore their alignment and orientation.

Figure 3:
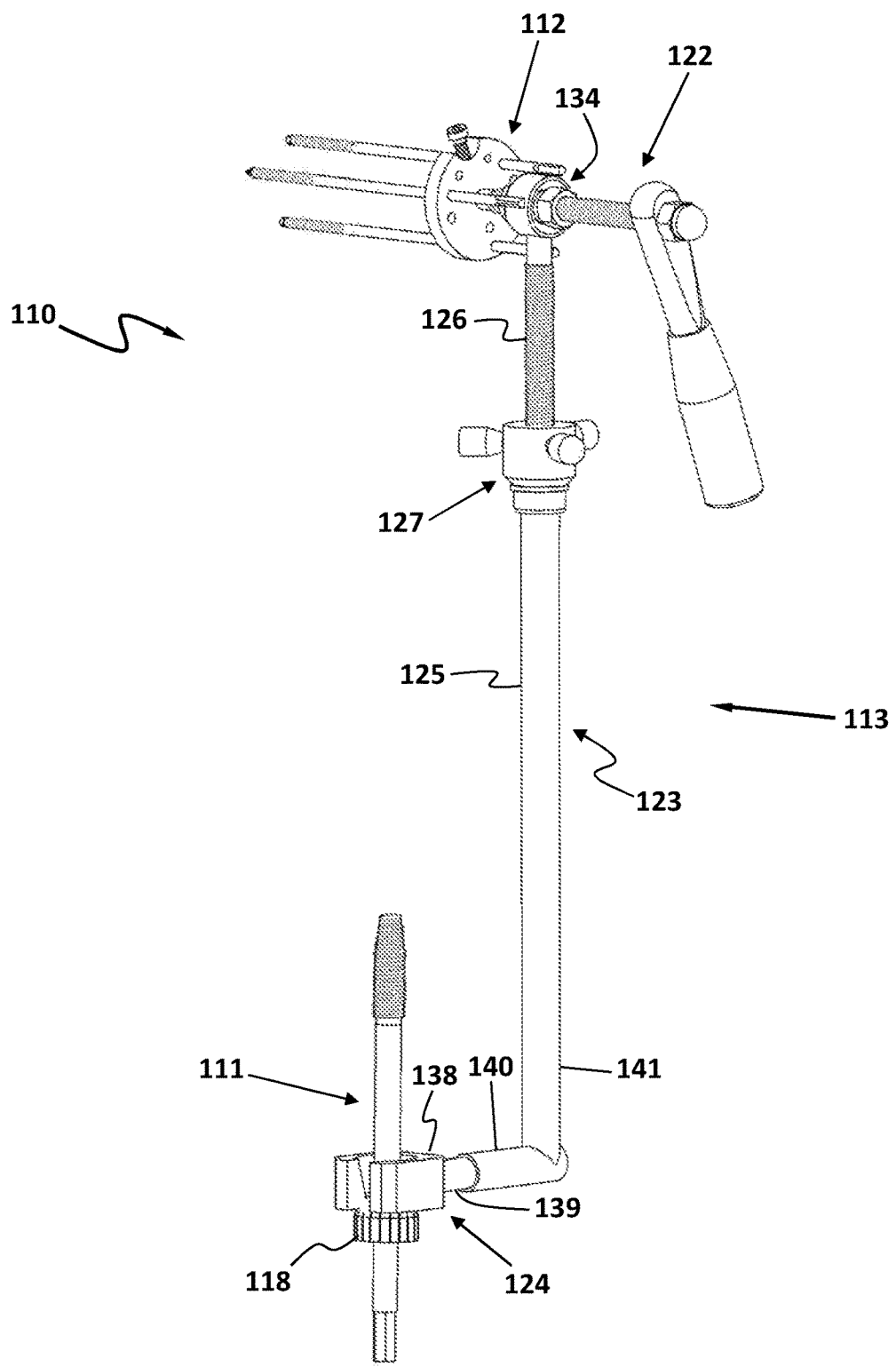
FIG. 3 shows an example of the orthopedic reduction device, according to one or more aspects of the present disclosure.

FIG. 3 illustrates an exemplary implementation of an orthopedic reduction device 110, according to one or more aspects of the present disclosure. Device 110 may include proximal attachment member 111 that may be configured to be coaxially attached and fixed to a proximal fragment of a fractured bone; distal attachment member 112 that may be configured to be attached and fixed to a distal fragment of a fractured bone; and distracting mechanism 113 that may be coupled to proximal attachment member 111 from its proximal end and to distal attachment member 112 from its distal end and may be configured for manipulating the proximal and distal fragments of the fractured bone in order to restore their alignment and orientation (i.e., fracture reduction).

Figure 4:
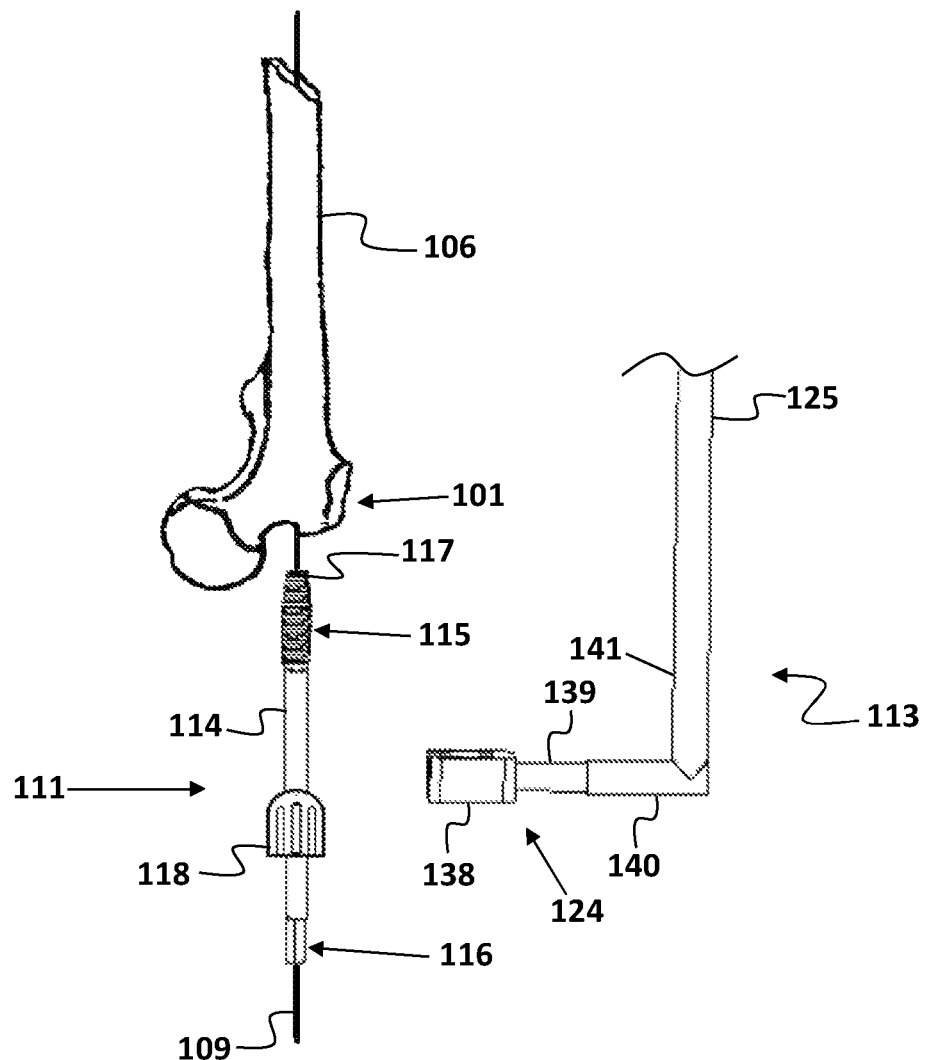
FIG. 4 shows an exemplary implementation of a proximal attachment member, according to one or more aspects of the present disclosure.

Referring to FIG. 4, proximal attachment member 111 may a cannulated screw 114 having a cylindrical canal in the middle (not explicitly shown in FIG. 4) that may be screwed over guide wire 109 into proximal end 101 of the fractured bone, thereby being coaxially fixed to proximal fragment 106. Such a coaxial proximal fixation to the bone may allow for a dynamic distraction of proximal fragment 106 without incuring extra injury to the tissue and since canullated screw 114 may be screwed over guide wire 109, the medullary canal may be accessible during distraction. Cannulated screw 114 may include threaded segment 115 at its distal end and wrenching segment 116 at its proximal end.

In an implementation, tapper 117 may be formed on the distal end of cannulated screw 114 at the tip of threaded segment 115. Tapper 117 may be configured to create taps in the cancellous bone of the proximal metaphysis as cannulated screw 114 is being driven inside the proximal end 101 of the fractured bone. Creating taps in the cancellous bone utilizing tapper 117 may provide sufficient grip for the proximal attachment member 111 inside proximal end 101 of the bone.

In an implementation, wrenching segment 116 may be configured such that a wrench or any other driving devices may be coupled with the cannulated screw 114 and drive cannulated screw 114 into the proximal end 101 of the bone. Wrenching segment 116, in an aspect allows for using a wrench or a driving device to rotate cannulated screw 114 back and forth to create taps in the bone to the desired depth.

According to another implementation, support 118 may be formed near the proximal end of cannulated screw 114, above wrenching segment 116. In an implementation, support 118 may be formed integral with cannulated screw 114 and it may be configured as an engagement point, on which distracting mechanism 113 may be engaged with proximal attachment member 111. In an implementation, support 118 may be formed as a semi-sphere facing downwards in the proximal third of cannulated screw 114.

Figure 5:
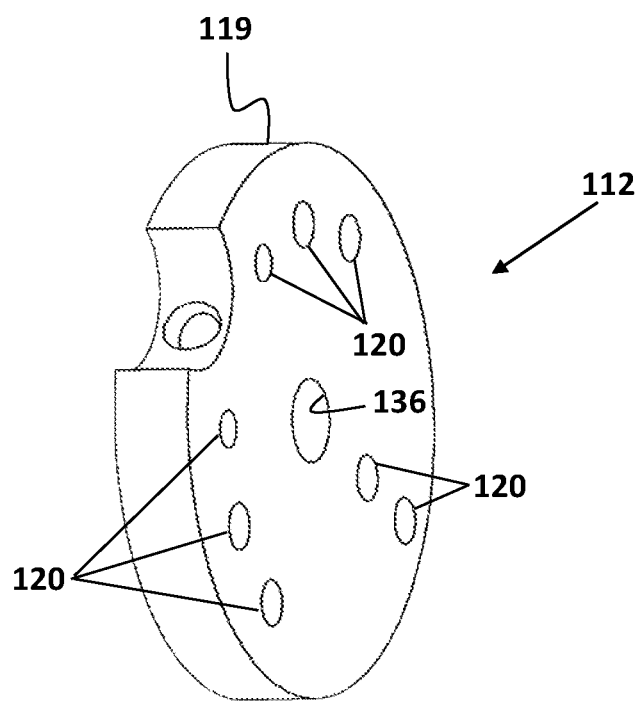
FIG. 5 illustrates an example of a distal attachment member, according to one or more implementations of the present disclosure.
Figure 6:
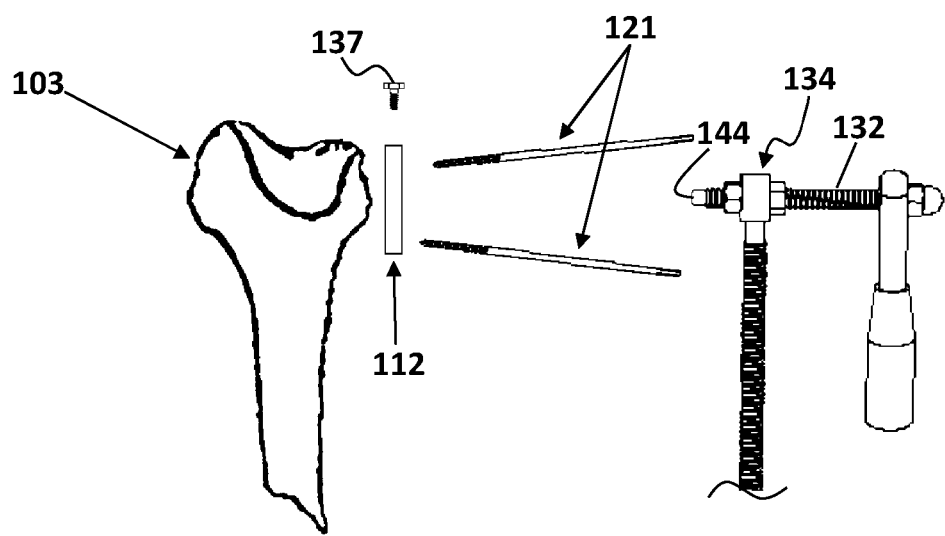
FIG. 6 illustrates an exemplary implementation of a distal attachment mechanism, according to one or more aspects of the present disclosure.

Referring to FIGS. 5 and 6, distal attachment member 112 may be a plate 119 with a number of through holes 120 thereon. Through holes 120 may have different diameters corresponding to standard orthopedic screws. Orthopedic screws 121 may be driven through holes 120 into the lateral side of distal end 103 of the bone, thereby attaching and fixing plate 119 on distal end 103 of the bone. In an implementation, distal attachment member 112 may be configured as a disk, as shown in FIG. 5.

Referring to FIG. 3, distracting mechanism 113 may include distal manipulating handle 122 that may be coupled with the distal attachment member 112; extendable body 123; and proximal engagement member 124 that may be configured to engage proximal attachment member 111. According to an implementation, extendable body 123 may include fixed arm 125 that may an L-shaped sleeve; extendable arm 126 that may be movable inside fixed arm 125; and adjustment nut 127 that may be configured as a handle-shaped nut configured to allow for telescopic adjustment of the length of extendable body 123.

Figure 7:
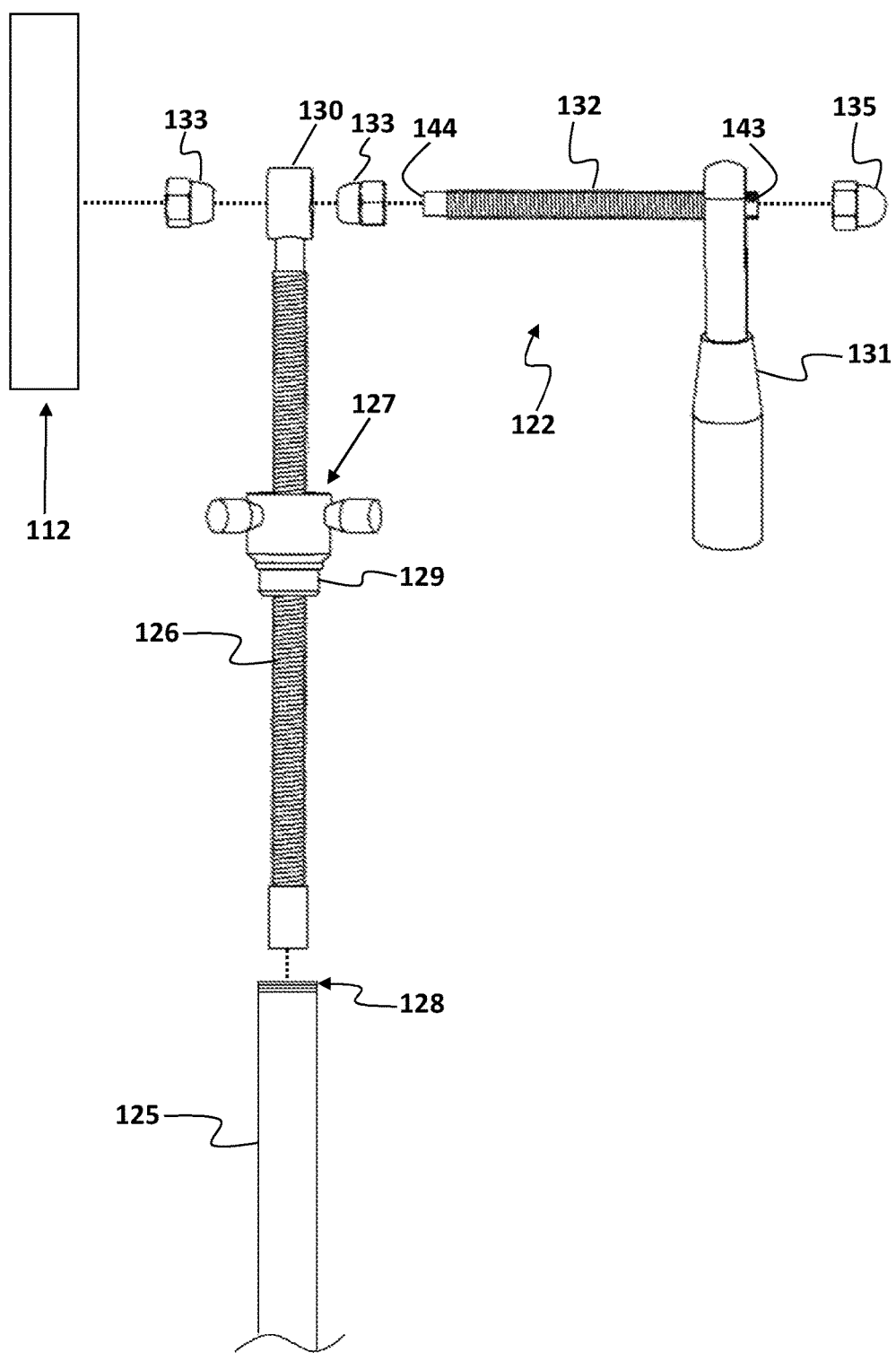
FIG. 7 illustrates an exploded view of a distracting mechanism of the orthopedic device, according to exemplary implementations of the present disclosure.

Referring to FIG. 7, in an implementation, extendable arm 126 may be a threaded rod on which adjustment nut 127 may be threaded. Adjustment nut 127 may sit on distal end 128 of fixed arm 125 and in an implementation thrust ball bearing 129 may be placed between nut 127 and distal end 128 of fixed arm 125. Extendable arm 126 may be configured to be telescopically movable within fixed arm 125 and its movement may be adjusted utilizing adjustment nut 127, such that rotating adjustment nut 127 urges extendable arm 126 to move out of fixed arm 125 and thereby increase the length of extendable body 123 (labeled in FIG. 3). In an implementation, extendable arm 126 may be configured with ring 130 at its distal end. Ring 130 may be formed integral with the distal end of extendable arm 126.

Referring to FIG. 7, distal manipulating handle 122 may include hand grip 131 and handle rod 132. Distal manipulating handle 122 may be configured to be articulated at the distal end of extendable arm 126. In an implementation, handle rod 132 may pass through ring 130 and two cap nuts 133 having threaded through holes may be threaded on handle rod 132 at either sides of ring 130. Ring 130 and two cap nuts 133 form a joint 134 (labeled in FIGS. 3 and 6) that may allow for manipulating handle 122 to articulate with extendable arm 126. Joint 134 may allow for free rotational movement of the handle rod 132 about roll, pitch and yaw axes. Proximal end 143 of handle rod 132 may be connected to hand grip 131 using, for example cap nut 135 and distal end 144 of handle rod 132 may be coupled with distal attachment member 112. Referring to FIGS. 5 and 6, distal end 144 of handle rod 132 may be placed in central hole 136 of distal attachment member 112 and it may be locked in place by, for example set screw 137.

Referring to FIGS. 3 and 4, proximal engagement member 124 may be configured as an open jaw that may sit on and engage with support 118. In an implementation, proximal engagement member 124 may include open jaw 138 connected to shaft 139. Shaft 139 may be slidably movable within horizontal portion 140 of fixed arm 125 allowing for horizontal adjustments in the distance between open jaw 138 and vertical portion 141 of fixed arm 125. A set screw may be utilized to lock shaft 139 in place once the adjustments are made.

Figure 8:
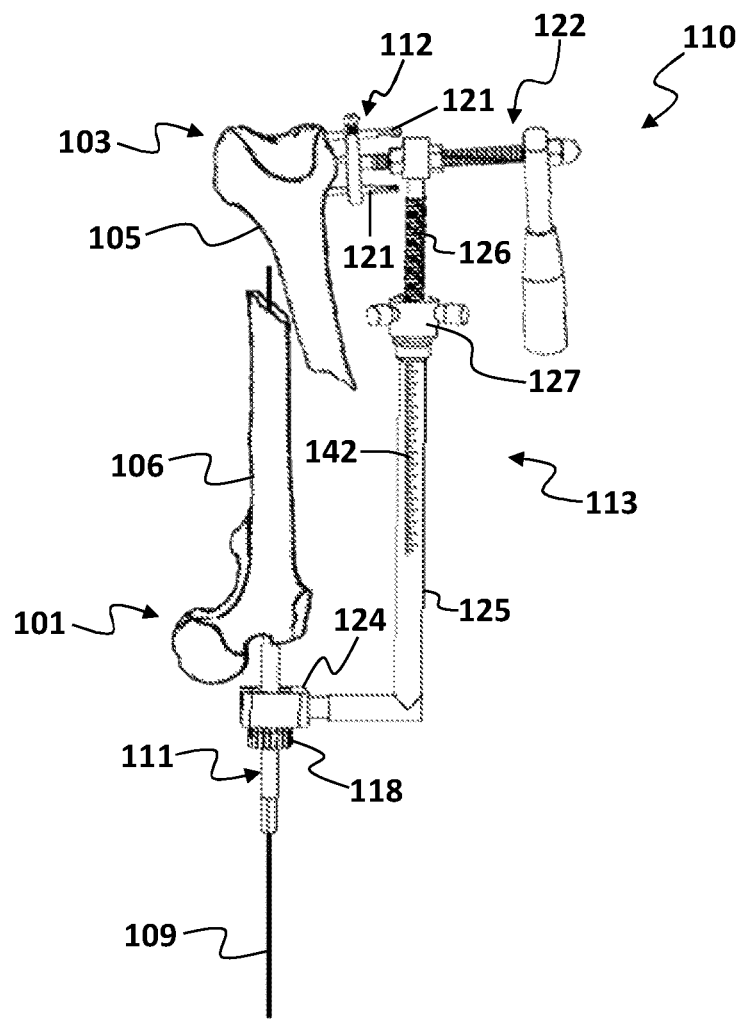
FIG. 8 shows an example of an orthopedic reduction device attached to an exemplary fractured bone, according to one or more aspects of the present disclosure.
Figure 9:
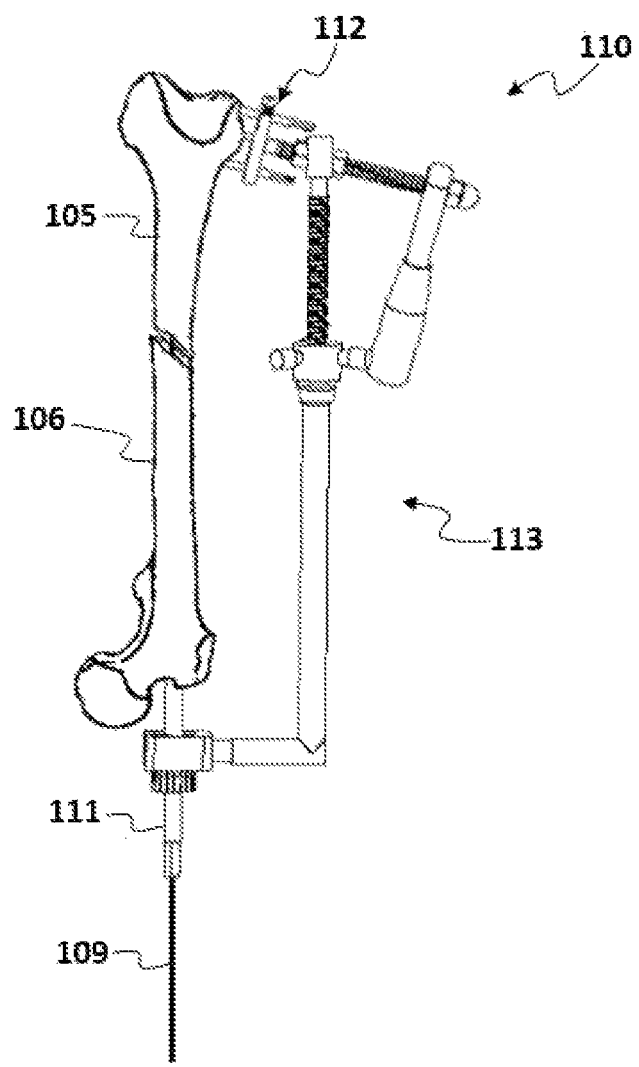
FIG. 9 shows the orthopedic reduction device attached to the exemplary fractured bone of FIG. 8 after reduction procedure, according to one or more aspects of the present disclosure.

FIGS. 8 and 9 illustrate an exemplary reduction procedure performed by methods and devices as described in this disclosure. Referring to FIG. 8, in an example of a femur bone fracture, distal bone fragment 105 and proximal bone fragment 106 may be shortened in relation to one another due to overlapping of the proximal and distal fragments 106, 105. Shortening is described by the number of centimeters of overlap. As shown in FIG. 8, the proximal fragment 106 and the distal fragment 105 may further lose their alignment, which means the axis of the proximal and distal fragments 106, 105 are not parallel to one another. Furthermore, rotation may happen between the proximal fragment 106 and distal fragment 105. Therefore, the deformity after a bone fracture may have an overriding component, an angulating component, and a rotating component. The purpose of fracture reduction is to correct the overriding, angulating and rotating components of the deformity. FIG. 9 shows the bone fracture after reduction. Referring to FIG. 9, the orientation and alignment of the proximal and distal bone fragments 106, 105 are restored.

Figure 10:
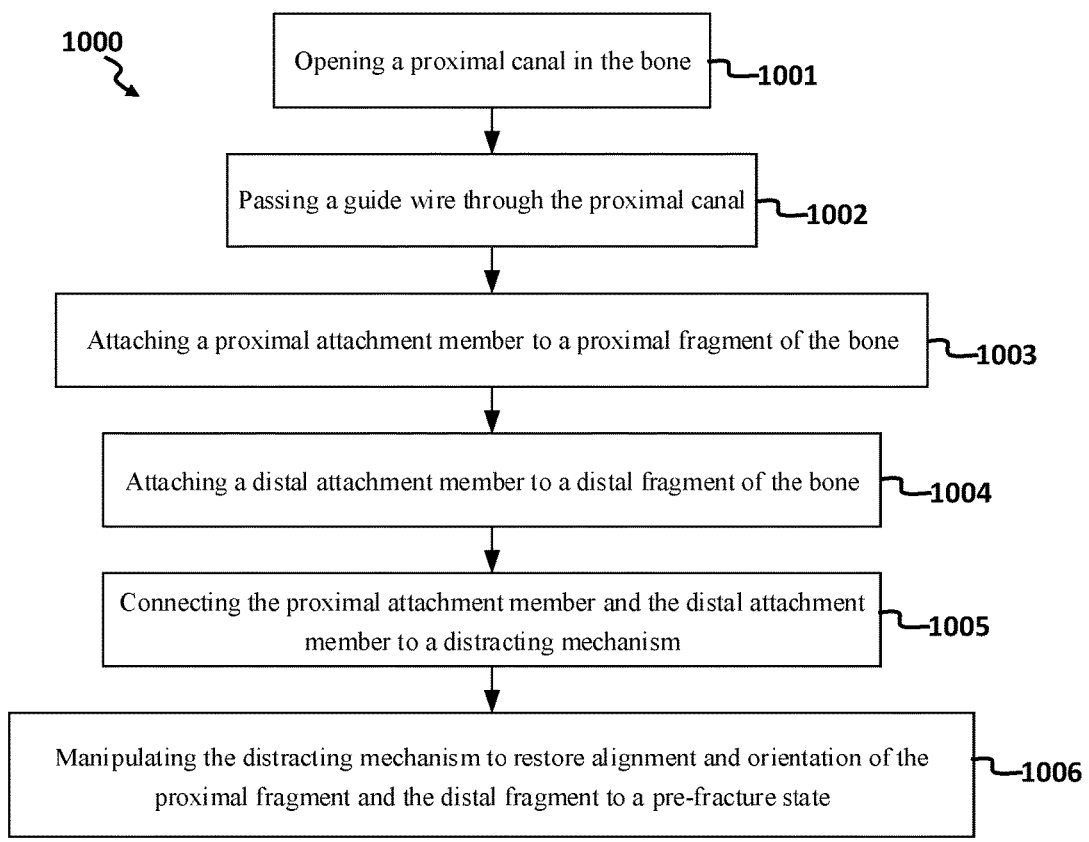
FIG. 10 illustrates an exemplary method for reducing a fracture, consistent with exemplary embodiment of the present disclosure.

FIG. 10 illustrates an exemplary method 1000 for reducing a fracture, consistent with exemplary embodiment of the present disclosure. The method 1000 may include: opening a proximal canal in the bone (step 1001); passing a guide wire through the proximal canal (step 1002); attaching a proximal attachment member to a proximal fragment of the bone (step 1003); attaching a distal attachment member to a distal fragment of the bone (step 1004); connecting the proximal attachment member and the distal attachment member to a distracting mechanism (step 1005); and manipulating the distracting mechanism to restore alignment and orientation of a the proximal fragment and the distal fragment to a pre-fracture state (step 1006).

As an illustration, referring to FIGS. 4, 8, and 10, in the exemplary step 1001, the proximal canal 108 may be opened by, for example an awl and a starting reamer. Moving on to step 1002, the guide wire 109 may be sent into the proximal canal 108. After that, in exemplary step 1003, the proximal attachment member 111 may be screwed over the guide wire 109 into proximal end 101 of the fractured bone and thereby coaxially fixed in place inside the proximal fragment 106.

With reference to FIGS. 6, 8, and 10, in exemplary step 1004, distal attachment member 112 may be placed on the lateral side of distal end 103 of distal fragment 105 and it may be fixed to the bone condyle by screwing in at least two orthopedic screws 121 into the bone through holes 120 on distal attachment member 112. In an implementation, orthopedic screws 121 may be screwed into the bone with an angle with respect with one another to achieve a better fixation. Moving on to step 1005, once both proximal and distal attachment members 111, 112 are attached and fixed to proximal and distal bone fragments 106, 105, distracting mechanism 113 may be connected to the distal and proximal members 111, 112. Moving on to step 1006, the surgeon may manipulate the distracting mechanism 113 to restore alignment and orientation of the proximal fragment 106 and distal fragment 105 to a pre-fractured state.

Referring to FIGS. 4 and 8, in order to reduce the fracture in a bone, first, the proximal canal 108 may be opened by, for example an awl and a starting reamer, then the guide wire 109 may be sent into the proximal canal 108. After that, the proximal attachment member 111 may be screwed over the guide wire 109 into proximal end 101 of the fractured bone and thereby coaxially fixed in place inside the proximal fragment 106. Referring to FIGS. 6 and 8, distal attachment member 112 may be placed on the lateral side of distal end 103 of distal fragment 105 and it may be fixed to the bone condyle by screwing in at least two orthopedic screws 121 into the bone through holes 120 on distal attachment member 112. In an implementation, orthopedic screws 121 may be screwed into the bone with an angle with respect with one another to achieve a better fixation. Once both proximal and distal attachment members 111, 112 are attached and fixed to proximal and distal bone fragments 106, 105, distracting mechanism 113 may be connected to the distal and proximal members 111, 112. Referring to FIG. 8, surgeon may adjust the length of the distracting mechanism by adjustment nut 127. Extendable arm 126 may be moved in and out of fixed arm 125 to adjust the length of distracting mechanism 113 according to the distance between proximal attachment member 111 and distal attachment member 112. Referring to FIGS. 5 and 6, after adjusting the length of distracting mechanism 113, handle rod 132 may be place inside central hole 136 of distal attachment member 112 and may be locked in place by set screw 137. Referring to FIG. 4, proximal engagement member 124 may be seated over support 118.

Referring to FIG. 8, once proximal and distal attachment members 111, 112 are attached and fixed to the proximal and distal fragments 106, 105 and distracting mechanism 113 is connected to both proximal and distal attachment members 111, 112, reduction device 110 is ready for performing fracture reduction procedure. In order to correct the overriding component of the deformity, the surgeon may turn adjustment nut 127. Turning adjustment nut 127 urges extendable arm 126 to move out of fixed arm 125 and thereby force bone fragments 105 and 106 to their normal position (i.e., distraction). Support 118 acts as an engagement point and the distracting force is transformed by proximal engagement member 124 to proximal attachment member 111 via support 118. In an implementation, fixed arm 125 and extendable arm 126 may include scale 142 thereon to help the surgeon figure out the acquired length of the fractured bone while distracting fragments 105, 106.

Since proximal attachment member 111 may be coaxially fixed inside proximal fragment 106, distracting force may also be exerted coaxially on proximal fragment 106 and therefore proximal fragment 106 may not lose its normal alignment and orientation during distraction. However, distal fragment 105 may be laterally angulated due to non-coaxial distraction force exerted on it via distal attachment member 112. At this stage, distal manipulating handle 122 may be utilized to restore the alignment and orientation of distal fragment 105. The surgeon may manipulate distal end 103 and simultaneously push guide wire 109 from proximal canal 108 into distal canal 107. Once bone fragments 105, 106 are aligned as shown in FIG. 9 guide wire 109 moves into distal canal 107 (labeled in FIGS. 2A and 2B) and makes a characteristic sound and sensation for the surgeon to realize that the reduction procedure is completed. Benefits form this feature may include, but are not limited to avoiding the exposure of x-ray radiation to the patient and staff, because the cannulated design of the proximal attachment member may allow the surgeon to manipulate the guide wire while reducing the bone fragments and may allow the surgeon to utilize the characteristic sound and sensation made by the guide wire to realize the alignment of the two bone fractures without the need for a fluoroscopy set.

Guide wire 109 may be kept in the medullary canal after the procedure is finished. Proximal attachment member 111 is opened and removed from proximal end 101 of the bone. Handle rod 132 may also be released form distal attachment member 112 and distracting mechanism 113 may be remove completely. Now the medullary canal is open for reaming by classic reaming instruments.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

What is claimed is:

1. A fracture reduction device for treating a fractured bone comprising a proximal fragment and a distal fragment, the device comprising:
    a proximal attachment member configured to be coaxially attached and fixed into the proximal fragment of the bone;
    a distal attachment member configured to be laterally attached and fixed to the distal fragment of the bone; and
    a distracting mechanism engaged with the proximal attachment member and coupled with the distal attachment member,
    wherein the distracting mechanism is configured to manipulate the proximal fragment and the distal fragment to restore their alignment and orientation to a pre-fracture state, and wherein the distracting mechanism comprising:
    an extendable body comprising a fixed arm and an extendable arm, wherein:
        the extendable arm is a threaded rod adjustably movable inside the fixed arm allowing for telescopically changing the length of the distracting mechanism;
        the fixed arm is an L-shaped configuration with a vertical portion and a horizontal portion, wherein the vertical portion is configured to telescopically receive the extendable arm therein, wherein the horizontal portion of the fixed arm is slidably attached to and configured to receive a proximal engagement member therein; and
        a flat surface of the distal attachment member, configured to be laterally attached and fixed to the distal fragment of the bone, is parallel to both the extendable arm and the vertical portion of the fixed arm.

2. The device according to claim 1, wherein the proximal attachment member is a cannulated screw with a cylindrical canal in the middle.

3. The device accordingly to claim 2, further comprising a guide wire passed through the cylindrical canal in the middle,
    wherein the proximal attachment member is screwed over the guide wire into the proximal fragment of the bone.

4. The device accord to claim 3, wherein a length of the guide wire extends from at least a bottom of the proximal attachment member to the distal attachment member.

5. The device according to claim 2, wherein the cannulated screw comprises a threaded segment in a distal end and a wrenching segment in a proximal end, wherein the threaded segment is configured to be screwed into the proximal segment of the bone, wherein the wrenching segment is configured to allow for utilizing a driving means to drive the cannulated screw in to the proximal segment of the bone.

6. The device according to claim 5, wherein a tapper is formed on the distal end of the cannulated screw.

7. The device according to claim 2, wherein the proximal attachment member further comprises a support configured as an engagement point for the distracting mechanism to engage the proximal attachment member.

8. The device according to claim 7, wherein the support is formed integral with the cannulated screw.

9. The device according to claim 1, wherein the distal attachment member comprises a plate with a plurality of holes thereon, wherein the holes are configured to allow for orthopedic screws to be driven into the distal fragment therethrough.

10. The device according to claim 1, wherein the distracting mechanism further includes:
    a distal manipulating handle coupled with the distal attachment member, thereby attached to the distal fragment;
    a proximal engagement member configured to engage the proximal attachment member, thereby attached to the proximal fragment,
    wherein, the distal manipulating handle is configured to be articulated with the extendable arm to manipulate the distal fragment.

11. The device according to claim 1, wherein the extendable body further comprises an adjustment nut threaded on the extendable arm configured to urge the extendable arm out of the fixed arm.

12. A method for reducing fracture in a bone, comprising:
    opening a proximal canal in the bone;
    passing a guide wire through the proximal canal;
    attaching a proximal attachment member to a proximal fragment of the bone, wherein the proximal attachment member comprises a cannulated screw;
    attaching a distal attachment member to a distal fragment of the bone by utilizing at least two orthopedic screws;
    connecting the proximal attachment member and the distal attachment member to a distracting mechanism; and
    manipulating the distracting mechanism to restore alignment and orientation of a the proximal fragment and the distal fragment to a pre-fracture state, the distracting mechanism comprising:
    an extendable body comprising a fixed arm and an extendable arm, wherein:

the extendable arm is a threaded rod adjustably movable inside the fixed arm allowing for telescopically changing the length of the distracting mechanism;

the fixed arm is an L-shaped configuration with a vertical portion and a horizontal portion, wherein the vertical portion is configured to telescopically receive the extendable arm therein, wherein the horizontal portion of the fixed arm is slidably attached to and configured to receive a proximal engagement member therein; and a flat surface of the distal attachment member, configured to be laterally attached and fixed to the distal fragment of the bone, is parallel to both the extendable arm and the vertical portion of the fixed arm.

13. The method of claim 12, wherein the cannulated screw comprises a cylindrical canal in the middle.

14. The method of claim 13, wherein attaching a proximal attachment member to a proximal fragment of the bone comprises passing the guide wire through the cylindrical canal in the middle.

* * * * *